United States Patent [19]

Miyano et al.

[11] Patent Number: 4,546,194
[45] Date of Patent: Oct. 8, 1985

[54] SUBSTITUTED CHROMANON-2-YL ALKANOLS AND DERIVATIVES THEREOF

[75] Inventors: Masateru Miyano, Northbrook; Clara I. Villamil, Glenview; Robert L. Shone, Palatine, all of Ill.

[73] Assignee: G. D. Searle & Co., Skokie, Ill.

[21] Appl. No.: 614,893

[22] Filed: May 29, 1984

[51] Int. Cl.$^4$ .......................................... C07D 311/04
[52] U.S. Cl. .................................................... 549/401
[58] Field of Search ........................................ 549/401

[56] References Cited

U.S. PATENT DOCUMENTS

| | | | |
|---|---|---|---|
| 3,862,175 | 1/1975 | Fitzmaurice et al. | 549/401 |
| 3,882,148 | 5/1975 | Augstein et al. | 549/401 |
| 3,948,955 | 4/1976 | Lee et al. | 549/403 |
| 4,133,889 | 1/1979 | Augstein et al. | 549/401 |
| 4,281,008 | 7/1981 | Chamberlain | 549/401 |

FOREIGN PATENT DOCUMENTS 0079637 11/1982 European Pat. Off. .

OTHER PUBLICATIONS

Chem. Abstracts 69: 85967t.
Griffin et al., "Effects of Leukotriene D on the Airways in Asthma," *N. Engl. J. Med.*, 308, 436–439 (1983).
Lewis & Austen, "Mediation of Local Homeostasis and Inflammation by Leukotrienes and Other Mast-Cell Dependent Compounds," *Nature*, 293, 103–108 (1981).
Michelassi et al., "Leukotrine $D_4$: A Potent Coronary Artery Vasoconstrictor Associated with Impaired Ventricular Contraction," *Science*, 217, 841–843 (1982).
Burke et al., "Leukotrienes $C_4$, $D_4$ and $E_4$: Effects on Human and Guinea-Pig Cardiac Preparations in Vitro," *J. Pharmacol. and Exp. Therap.*, 221, 235–241 (1982).
Schild, "pA, A New Scale for the Measurement of Drug Antagonism," *Brit. J. Pharmacol.*, 2, 189–206 (1947).
Tallarida & Murray, *Manual of Pharmacologic Calculations with Computer Programs*, (New York: Springer-Verlag, 1981), pp. 33–35.

*Primary Examiner*—Ethel G. Love
*Attorney, Agent, or Firm*—John J. McDonnell; Stuart L. Melton

[57] ABSTRACT

This invention relates to substituted chromanon-2-yl alkanols and derivatives thereof, which are useful as leukotriene $D_4$ ($LTD_4$) inhibitors and therefore useful in the treatment of allergies, inflammatory conditions, and coronary vasoconstriction.

25 Claims, No Drawings

SUBSTITUTED CHROMANON-2-YL ALKANOLS AND DERIVATIVES THEREOF

BACKGROUND OF THE INVENTION (a) Field of the Invention

This invention in its broadest aspect relates to inhibitors of metabolic pathways. In particular, the invention relates to novel compounds of Formula I, which are inhibitors of leukotriene $D_4$ ($LTD_4$) and which therefore are useful to prevent or alleviate the symptoms associated with $LTD_4$, such as allergic reactions, particularly asthma, see M. Griffin et al., *N. Engl. J. Med.*, 308, 436 (1983); inflammatory conditions; and coronary vasoconstriction.

$LTD_4$ is a product of the 5-lipoxygenase pathway and is the major active constituent of slow reacting substance of anaphylaxis (SRS-A), a potent bronchoconstrictor that is released during allergic reactions. See R. A. Lewis and K. F. Austen, *Nature*, 293, 103–108 (1981). When administered to humans and guinea pigs, $LTD_4$ causes bronchoconstriction by two mechanisms: (1) directly by stimulating smooth muscle; and (2) indirectly through release of thromboxin $A_2$, which causes contraction of respiratory smooth muscle. Because antihistamines are ineffective in the management of asthma, SRS-A is believed to be a mediator of the bronchoconstriction occurring during an allergic attack. $LTD_4$ may also be involved in other inflammatory conditions such as rheumatoid arthritis. Furthermore, $LTD_4$ is a potent coronary vasoconstrictor and influences contractile force in the myocardium and coronary flow rate of the isolated heart. See F. Michelassi et al., *Science*, 217, 841 (1982); J. A. Burke et al., *J. Pharmacol. and Exp. Therap.*, 221, 235 (1982).

(b) Prior Art

Certain 2-alkylated chromanon-2-yl derivatives have been disclosed in the prior art. European Patent Application No. 0079637 and U.S. Application Ser. No. 06/560355, the latter having the same assignees as the present invention, disclose 2-alkylated chromanon-2-yl alkanoic acids. Since none of the compounds claimed in the present invention possesses a carboxylic acid function, they are distinguishable from chromanon-2-yl alkanoic acids of the prior art.

By combination of elements disclosed and claimed, Ser. No. '355 appears also to disclose certain 2-alkylated chromanon-2-yl alkanediols and ketoalkanols related to those claimed herein. However, the particular combination of elements that are characteristic of this invention, particularly the 2-alkyl-2-ketoalkanols and 2-alkyl-2-alkanediols, are not described in the prior art, nor are enabling methods for the preparation of compounds of this invention described. As described in Ser. No. '355, the side-chain keto group (or a hydroxymethylene group subsequently formed by reduction of the keto group) must always be attached directly to the chromanone nucleus. (That is, in Formula I, below, Z must be attached directly to the 2-position of the chromanone nucleus, with no intervening methylene carbon atoms). The compounds of this invention always possess an intervening alkylene chain. Moreover, all prior art compounds in Ser. No. '355 having a side-chain ketone function must be formed as acylation products of 2-carboxychromanones and not of 2-alkylchromanones. In contrast, the compounds of this invention are formed by a ring closure (see Scheme A, below) that does not require a 2-carboxyl function and permits the ketone group to be separated from the chromanone ring.

SUMMARY OF THE INVENTION

The invention relates to compounds of Formula I:

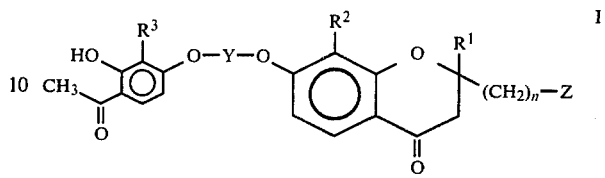

wherein Y is:

(a) —$(CH_2)_m$—

(b) —$(CH_2)_p$—CHOH—$(CH_2)_q$—

(c) —$(CH_2)_r$—CO—$(CH_2)_s$— wherein Z is:

(a)

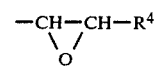

(b)

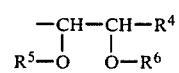

(c)

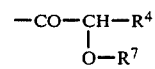

(d)

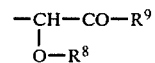

wherein $R^1$, $R^2$, and $R^3$ are alkyl of 1 to 6 carbon atoms, inclusive, each being the same or different; wherein $R^4$ is:

(a) hydrogen; or (b) alkyl of 1 to 6 carbon atoms, inclusive;

wherein $R^5$ and $R^6$, each being the same or different, are:

(a) hydrogen; or (b) alkanoyl of 2 to 6 carbon atoms, inclusive;

wherein $R^7$ and $R^8$ are:

(a) hydrogen; or (b) alkanoyl of 2 to 6 carbon atoms, inclusive;

wherein $R^9$ is alkyl of 1 to 6 carbon atoms, inclusive; wherein n is an integer from 1 to 10, inclusive; wherein m is an integer from 2 to 7, inclusive; wherein each of p and q is an integer from 1 to 5, inclusive, with the proviso that the sum (p+q) is no greater than 6; wherein each of r and s is an integer from 1 to 5, inclusive, with the proviso that the sum (r+s) is no greater than 6.

Examples of alkyl of 1 to 6 carbon atoms, inclusive, are methyl, ethyl, propyl, butyl, pentyl, hexyl, and the isomeric forms thereof, generally referred to as alkyl.

Examples of alkanoyl of 2 to 6 carbon atoms, inclusive, are acetyl, propanoyl, butanoyl, pentanoyl, and the isomeric forms thereof.

DESCRIPTION OF THE INVENTION

The compounds of this invention may be prepared by any of several methods known to those skilled in the art. For example, the particular sequence of reactions joining the aromatic rings through the linking group Y may be selected for synthetic convenience or for maximization of yields. The following Schemes illustrate some of the possible methods used to prepare the compounds of this invention. Compounds described below are typically purified by column chromatographic methods known to those skilled in the art.

Scheme A illustrates a method for preparing dihydropyranone intermediates of Formula VII.

SCHEME A

Base-catalyzed condensation of 3-substituted dihydroxyacetophenones of Formula II and alkenones of Formula III affords alkenyl-substituted dihydrobenzopyranones of

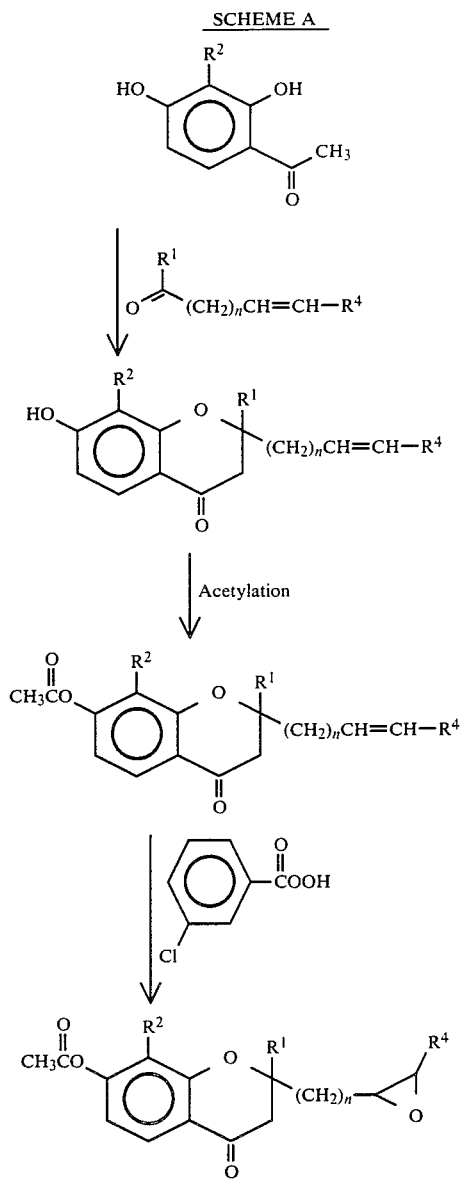

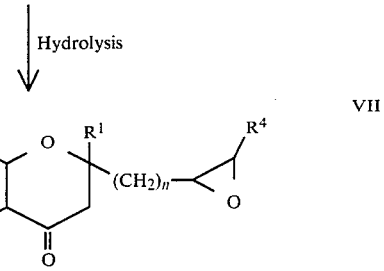

Formula IV. Preferred condensation conditions include heating the compounds at reflux in an unreactive organic solvent, such as toluene, with provision, such as a Dean-Stark trap, for removing water that is formed during the condensation. After the second phenolic hydroxyl function is protected, for example by acetylation to form compound V, the alkenyl function can be epoxidized to the intermediate compound of Formula VI. A preferred acetylation method employs acetic anhydride in pyridine. A preferred epoxidation method employs m-chloroperbenzoic acid in an unreactive organic solvent, such as dichloromethane. Basic hydrolysis then is used to remove the acetyl protecting group, affording the intermediate, Formula VII. Preferred hydrolysis conditions include stirring with potassium carbonate or sodium carbonate in methanol.

Scheme B illustrates an alternative method of preparing intermediates of Formula V (see Scheme A).

SCHEME B

Alkenyl compounds of Formula VIII (that is, Formula IV where $R^4$ is hydrogen) may be oxidatively cleaved to the aldehyde, Formula IX. One method for this cleavage employs sodium periodate and osmium tetroxide in an organic solvent such as t-butyl alcohol or dioxane. An ylide or Wittig reaction converts the aldehyde to the extended alkenyl intermediate, Formula V (where $R^4$ is alkyl). A preferred method involves converting an alkyltriphenylphosphonium halide salt to the

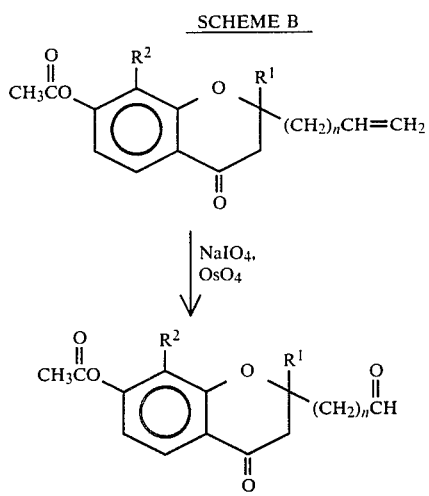

-continued
SCHEME B

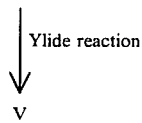

phosphorane reagent by reaction with a strong base, such as butyllithium, in an inert solvent. The phosphorane thus formed may be diluted with a cold solvent, such as dimethylsulfoxide at −20°, where it is allowed to react with the aldehyde.

Scheme C illustrates a method for joining the two aromatic moieties of the compounds of this invention.

SCHEME C

Alkylation of 3-substituted dihydroxyacetophenones of Formula X with omega-bromoalkanols affords intermediates of Formula XI. A preferred method employs phase-transfer conditions: the reactants are stirred at reflux in a mixture of tetrabutylammonium hydrogen sulfate, aqueous sodium hydroxide, and dichloromethane. The resultant intermediates of Formula XI are coupled with compounds of Formula VII (see Scheme A) to form compounds of this invention, Formula XII. A preferred condensation method employs triphenylphosphine and diethyl azodicarboxylate in an unreactive organic solvent, such as tetrahydrofuran. Compounds in Formula XII may be used to prepare other compounds of this invention. For example, the epoxide function can be ring-opened by reaction with sodium acetate in acetic acid to form acetoxy alcohols of this invention, Formulas XIII and XIV. Other acylated compounds of this invention may similarly be prepared. The position isomers may be separated, for instance by chromatogaphic techniques, or they may be used as a mixture in subsequent reactions, after

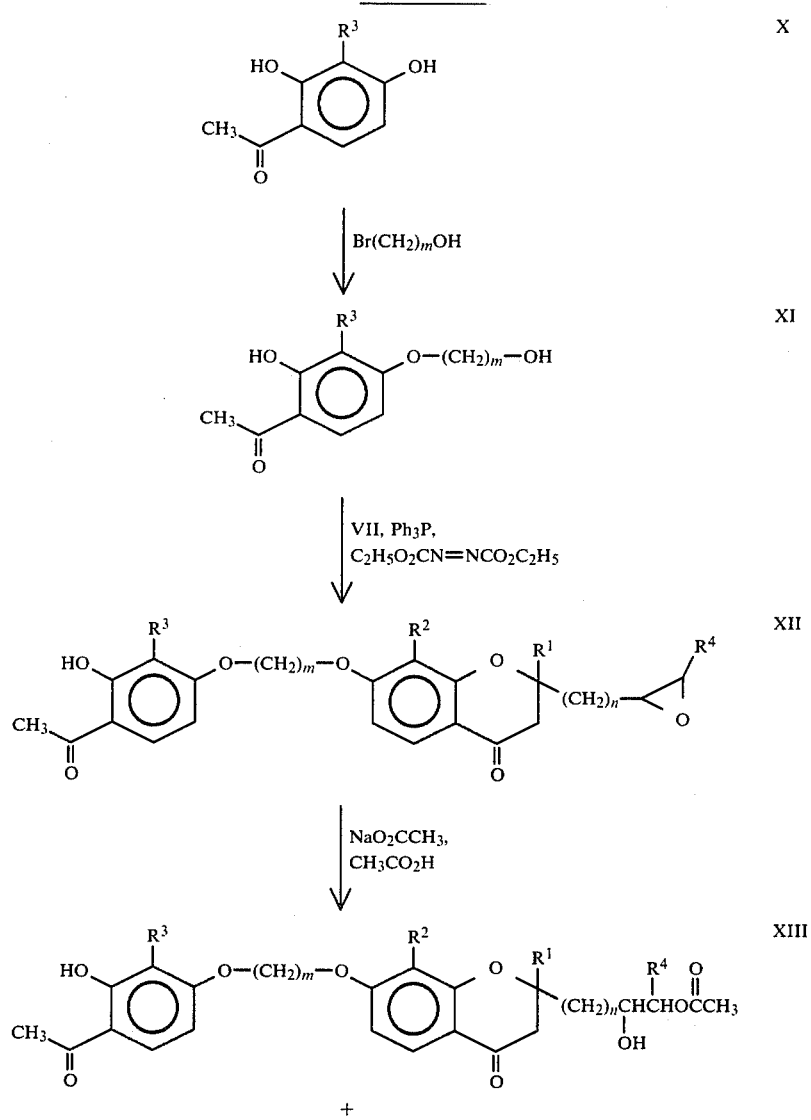

SCHEME C -continued

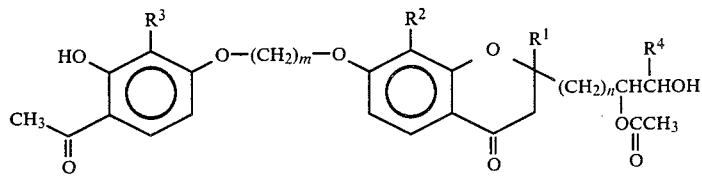

which the resultant product compounds may be separated. Schemes E through G illustrate further elaboration of the compounds of this invention derived from compounds of Formulas XIII and XIV.

Scheme D illustrates one of the possible subsequent reactions to form other compounds of this invention.

in pure form, is subjected to oxidation conditions which will form the ketone of Formula XVI. A preferred oxidation method employs Jones reagent (an adduct of chromic anhydride and aqueous sulfuric acid used in acetone solution). Removal of the acetyl group by hydrolysis under basic conditions, such as potassium carbonate in methanol, affords a ketoalcohol of Formula XVII.

SCHEME D (XIII + XIV)

| Hydrolysis

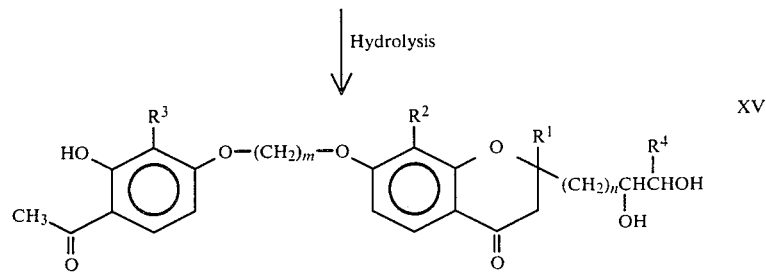

SCHEME E

XIII

| Jones oxidation

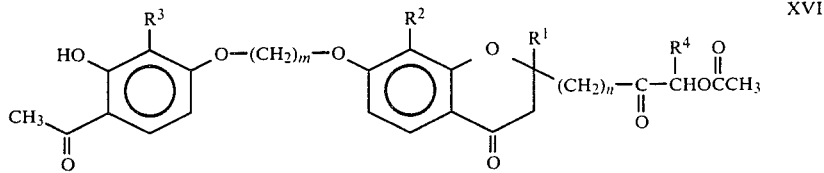

| Hydrolysis

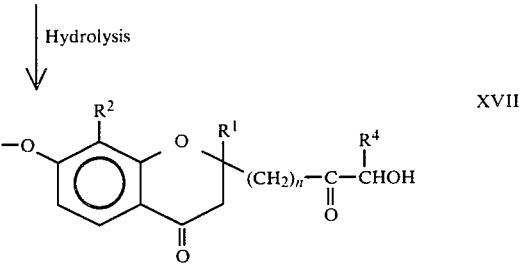

The individual compounds of Formulas XII and XIV or a mixture of the unseparated compounds may be hydrolyzed to give a dihydroxy compound of Formula XV. A preferred hydrolysis method employs lithium hydroxide in aqueous methanol.

Scheme E illustrates one method for preparing ketones of this invention.

SCHEME E

An acetoxy alcohol compound of Formula XIII, employed either in a mixture with a compound XIV or Under the conditions described in Scheme E, some of the compounds of Formula XIV will oxidize to different products from those of Formula XIII, as shown in Scheme F.

SCHEME F

Where $R^4$ is alkyl, Jones oxidation will transform compounds of Formula XIV to acetoxy ketones of Formula XVIII, which are position isomers of compounds of Formula XVI (see Scheme E). Basic hydrolysis, as described in Scheme E, will convert acetoxy ketones XVIII to corresponding ketoalcohols, Formula XIX. Where $R^4$ is hydrogen, however, Jones oxidation will transform compounds of Formula XIV all the way to carboxylic acids of Formula XX. (Note that the mixture of Jones oxidation products formed from a mixture of acetoxy alcohols XIII and XIV can thus initially be separated by extraction of carboxylic acid XX into aqueous base.) Basic hydrolysis followed by acidification will afford the corresponding alcohols, Formula XXI.

As shown in Scheme G, milder oxidation of compounds of Formula XIV, where $R^4$ is hydrogen, affords aldehydes of Formula XXII rather than carboxylic acids.

SCHEME G

A preferred milder oxidation method employs Collins reagent (a complex of chromic anhydride and two equivalents of pyridine)

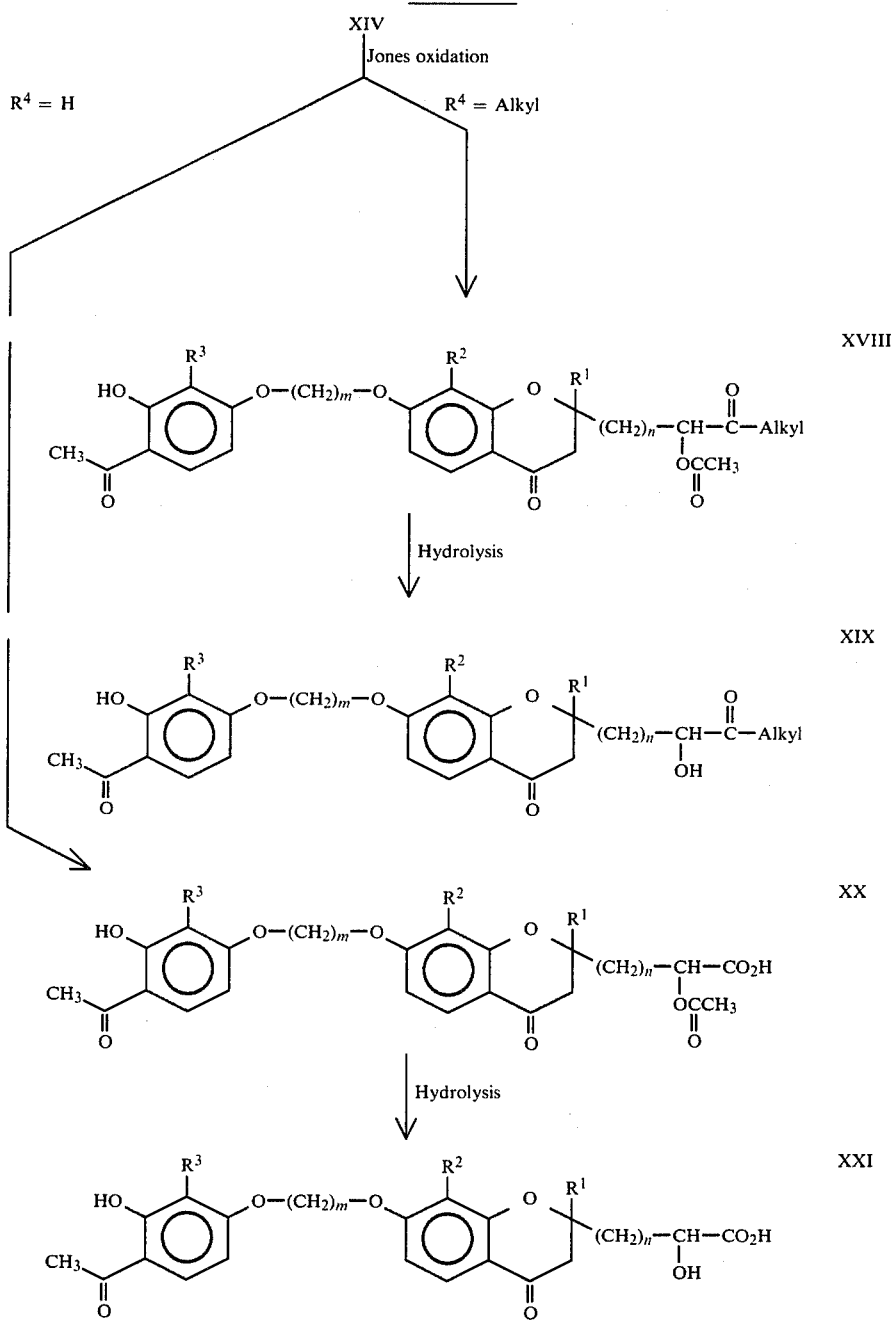

SCHEME G

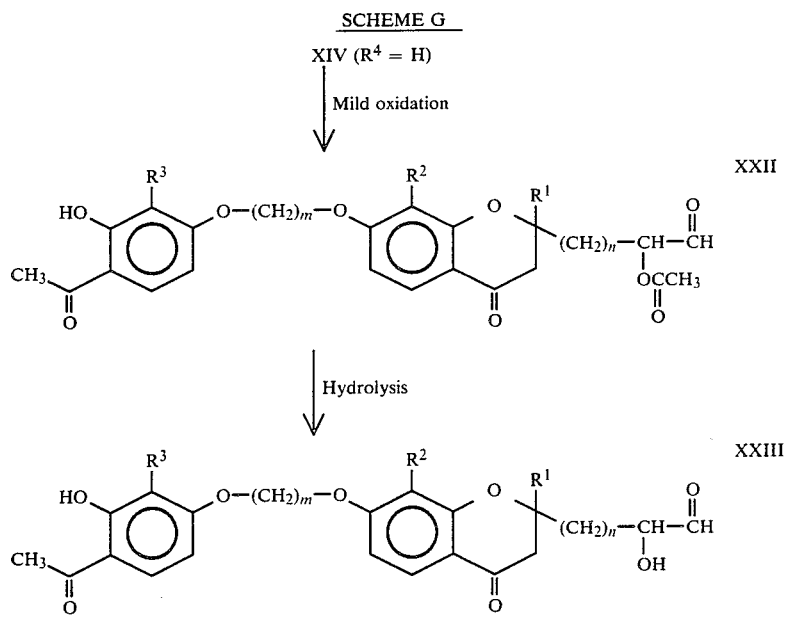

in an unreactive organic solvent, such as dichloromethane, at approximately 0° to 25° C. Alternatively, oxidation with pyridinium chlorochromate in dichloromethane at room temperature also affords aldehydes. As described before, basic hydrolysis of the acetoxy compounds. Formula XXII, affords corresponding alcohols of Formula XXIII.

Compounds of this invention having an alcohol or ketone group in the bridging group Y (see Formula I) are prepared by somewhat different methods from those described above in Schemes A through G. Scheme H illustrates one general method.

SCHEME H

Epoxy acetophenone derivatives of Formula XXIV react with alkenyl-substituted dihydropyranones of Formula IV (see Scheme A) to form compounds of Formula XXV, in which the bridging chain possesses a hydroxyl functionality. Preferred reaction conditions included heating the compounds with a base, such as benzyltrimethylammonium hydroxide, in a polar organic solvent, such as dimethylformamide, at 110°–120° for about two days. The alkenyl function may then be converted to the corresponding diol, thereby forming compounds of this invention, Formula XXVI. A preferred method employs N-methylmorpholine N-oxide and a catalytic amount of osmium tetroxide in an aqueous t-butyl alcohol-acetone solution. Compounds of Formula XXVI in which $R^4$ is hydrogen may conveniently be converted to keto compounds of Formula XXVIII. The primary hydroxyl group is

SCHEME H

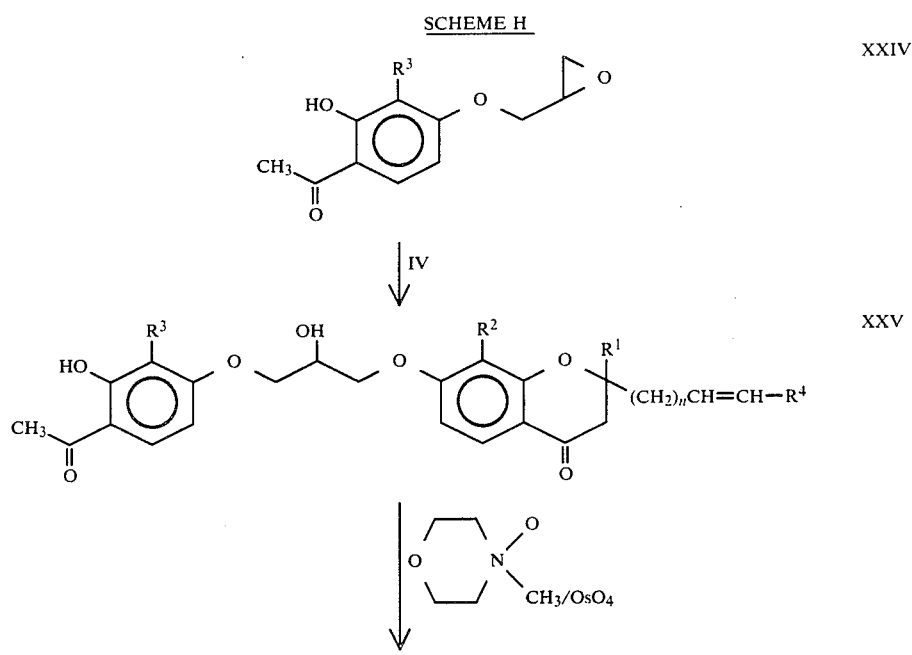

-continued
SCHEME H

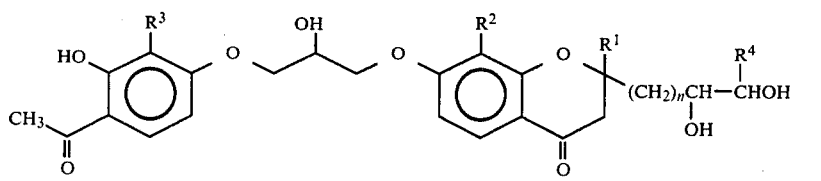    XXVI

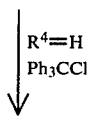

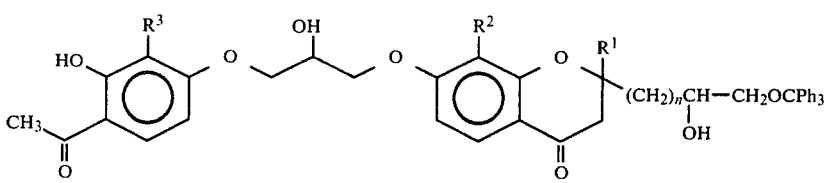    XXVII

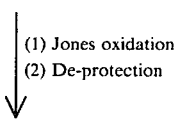

(1) Jones oxidation
(2) De-protection

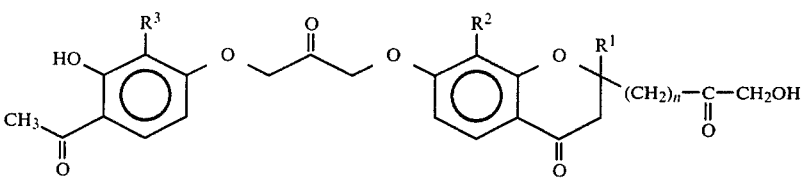    XXVIII selectively protected before oxidation. A preferred protecting group is triphenylmethyl (trityl), which forms the ether shown in Formula XXVII by reaction of compounds XXVI with trityl chloride in dry pyridine. Subsequent Jones oxidation, as described above (see Schemes E and F), and removal of the trityl group under acid conditions, preferably 90% aqueous trifluoroacetic acid in t-butyl alcohol, affords compounds of this invention, Formula XXVIII. This latter method of oxidizing the protected compounds of Formula XXVII may also be used to convert compounds of Formula XV (see Scheme D) to compounds of Formula XVII (see Scheme E), although in each case $R^4$ is preferably hydrogen.

The preferred embodiments of this invention include compounds of the following general structure, Formula XXIX.

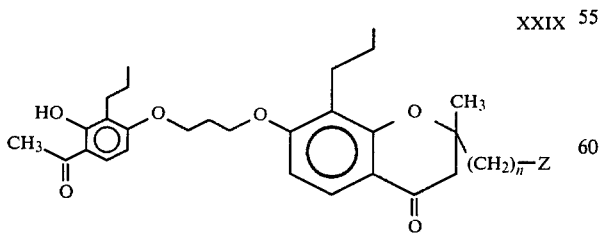    XXIX

More specifically, the preferred embodiments include compounds of Formula XXIX wherein Z is the following:

(a) 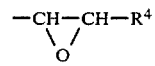

(b) 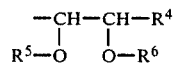

(c) 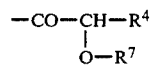

(d) 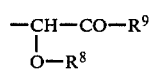

wherein $R^4$ is hydrogen or lower alkyl (that is, consisting of 1 to 6 carbon atoms, inclusive); wherein $R^5$ and $R^6$ are both hydrogen, or one of $R^5$ and $R^6$ is hydrogen and the other is lower alkanoyl (that is, consisting of 2 to 6 carbon atoms, inclusive); wherein $R^7$ and $R^8$ are hydrogen or lower alkanoyl; wherein $R^9$ is lower alkyl; and wherein n is an integer from 2 to 4.

The most preferred embodiments of this invention include compounds of the following general structure, Formula XXX.

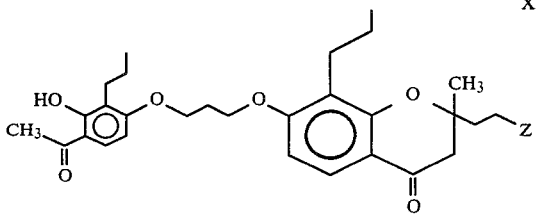
XXX

More specifically, the preferred embodiments include compounds of Formula XXX wherein Z is the following:

(a)

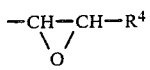

(b)

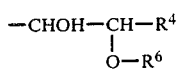

(c)

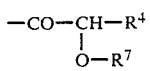

wherein $R^4$ is hydrogen or lower alkyl (that is, consisting of 1 to 6 carbon atoms, inclusive); wherein $R^6$ is hydrogen or lower alkanoyl (that is, consisting of 2 to 6 carbon atoms, inclusive); and wherein $R^7$ is hydrogen or lower alkanoyl.

The compounds of this invention exhibited antiallergy activity in guinea pigs, as indicated by antagonism in vitro (isolated ileum segments) of $LTD_4$-induced smooth muscle contractions and by antagonism in vivo of $LTD_4$-induced bronchoconstriction. The antiallergy activity of the compounds of this invention illustrated in the examples was tested by the following methods.

ANTAGONISM OF $LTD_4$-INDUCED SMOOTH MUSCLE CONTRACTIONS

Segments of ileum tissue isolated from guinea pigs were mounted in a modified Tyrode solution (8.046 g/l of sodium chloride, 0.200 g/l of potassium chloride, 0.132 g/l of calcium chloride monohydrate, 0.106 g/l of magnesium chloride hexahydrate, 1.00 g/l of sodium bicarbonate, 0.058 g/l of sodium dihydrogen phosphate, and 1.00 g/l of dextrose) containing 0.1 mcg/ml atropine sulfate and 1.0 mcg/ml of pyrilamine maleate and aerated at 37° C. with 95% oxygen and 5% carbon dioxide. The tissue segments were stimulated with two or more concentrations of either $LTD_4$ or bradykinin triacetate (agonists), producing reproducible muscle contractions. The control solution was replaced by a solution or suspension of test compound ($1.0 \times 10^{-5}$M) and incubated for 30 minutes. Each agonist was again introduced to the appropriate solutions and increased doses were added, if necessary, until contractions were approximately equal to those of the previously determined controls or until excessive quantities of agonist were added. For each combination of test compound and agonist, the following dose ratio was calculated: the ratio of agonist concentration in the presence of test compound to the agonist concentration in the absence of test compound that will produce the same contractile response. A concentration of test compound was considered active if it produced a dose ratio against $LTD_4$ significantly ($P<0.05$) greater than a dose ratio obtained in a series of blank treatment tests. (Duplicate tests were conducted for each concentration of test compound, and third tests were conducted if the first two tests were inconsistent.) Compounds that were active against $LTD_4$ but not against bradykinin triacetate were considered selective $LTD_4$ antagonists.

A further measure of receptor affinity, $pA_2$, was also determined for selective $LTD_4$ antagonists. A $pA_2$ value is defined as the negative logarithm of the molar concentration of the antagonist which produces a dose ratio of 2. The $pA_2$ values were calculated by the method of Arunlakshana and Schild, Br. J. Pharmacol., 2, 189 (1947), using Schild plot slopes constrained to $-1$. See R. J. Tallarida and R. B. Murray, Manual of Pharmacologic Calculations with Computer Programs (New York: Springer-Verlag, 1981), pp. 33–35.

ANTAGONISM OF $LTD_4$-INDUCED BRONCHOCONSTRICTION

Fasted adult male Hartley guinea pigs weighing 300 to 350 grams were used in this assay. All test animals were pretreated with propranolol and pyrilamine to block the bronchoconstrictive effects of endogenous epinephrine and histamine, respectively, and with indomethacin to block the synthesis of thromboxane $A_2$. The animals were anesthetized with pentobarbital and attached to a rodent respirator. Continuous measurements of intratracheal insufflation pressure were obtained through an intratracheal pressure transducer. After a baseline record was obtained, $LTD_4$ (200 ng) was administered intravenously and agonist-induced changes in intratracheal insufflation pressure were measured. Compounds which antagonize the direct component of $LTD_4$ action on respiratory smooth muscle inhibit intratracheal insufflation pressure increases caused by $LTD_4$. To determine the effect of test compounds on $LTD_4$-induced bronchoconstriction, the compounds were administered to the animals either intravenously (10 mg per kg body weight) or intragastrically (100 mg per kg of body weight) at an appropriate interval prior to the $LTD_4$ challenge. Test compounds were rated active if intratracheal insufflation pressure was significantly ($P<0.05$) reduced relative to vehicle control animals, as assessed by a Student's one-tail t-test.

By virtue of their activity as $LTD_4$ antagonists, the compounds of Formula I are useful in treating asthma and other anaphylactic conditions, inflammation, and coronary vasoconstriction in mammals. A physician or veterinarian of ordinary skill can readily determine whether a subject exhibits one of these conditions. The preferred utility relates to treatment of asthma. Regardless of the route of administration selected, the compounds of the present invention are formulated into pharmaceutically acceptable dosage forms by conventional methods known to those skilled in the art.

The compounds may be administered in a number of dosage forms. A preferred method of delivery would be oral or a means that would localize the action of the drug. For example, for asthma the compounds could be inhaled using an aerosol or other appropriate spray. For an inflammatory condition such as rheumatoid arthritis the compounds could be injected directly into the affected joint. The compounds can also be administered in such oral dosage forms as tablets, capsules, pills, powders, or granules. They may also be administered intravascularly, intraperitoneally, subcutaneously, or intramuscularly, using forms known to the pharmaceutical art. In general, the preferred form of administration is oral. An effective but non-toxic quantity of the compound is employed in treatment. The dosage regimen for preventing or treating the conditions with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the disease state. In so proceeding, the physician or veterinarian could employ relatively low doses at first and subsequently increase the dose until a maximum response is obtained. Dosages of the compounds of the invention are ordinarily in the range of 0.1 to 10 mg/kg up to about 50 mg/kg orally.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

DESCRIPTION OF THE EMBODIMENTS

EXAMPLE 1

2-(3-butenyl)-3,4-dihydro-7-hydroxy-2-methyl-8-propyl-2H-1-benzopyran-4-one

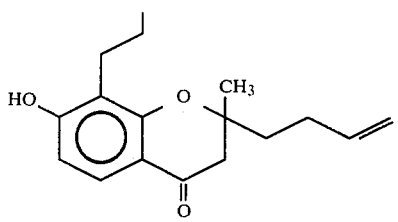

A mixture of 25 g (129 mmole) of 2,4-dihydroxy-3-propylacetophenone, 15 ml (ca. 129 mmole) of 5-hexen-2-one, and 5.4 ml (64 mmole) of pyrrolidine in 160 ml of toluene was heated at reflux for six hours under a Dean-Stark trap. Upon cooling, the reaction mixture was diluted with ethyl acetate and washed successively with water, 2N hydrochloric acid, and water. The organic phase was dried over magnesium sulfate, filtered, and concentrated in vacuo to a residue that crystallized upon standing. The crude solid was triturated with hexane and collected by filtration. Further purification by high performance column chromatography on silica gel (using 10% by volume ethyl acetate-toluene as eluent) afforded 23.5 g of the title compound as an analytically pure solid, m.p. 97.5°–98.5°. nmr (CDCl$_3$): δ (ppm) 0.96 (t, 3H, propyl CH$_3$); 1.38 (s, 3H, 2-methyl CH$_3$); 4.98 (m, 2H, alkenyl CH$_2$); 5.75 (m, 1H, alkenyl CH); 6.52, 7.72 (sets of d's, aromatic)

Analysis calcd. for C$_{17}$H$_{22}$O$_3$: C, 74.42; H, 8.08. Found: C, 74.47; H, 8.14.

EXAMPLE 2

7-acetoxy-2-(3-butenyl)-3,4-dihydro-2-methyl-8-propyl-2H-1-benzopyran-4-one

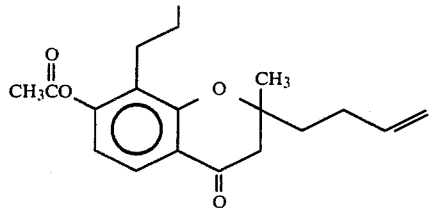

To 4.0 g of the title product of Example 1 in 25 ml of pyridine was added 3.0 ml of acetic anhydride. Upon completion of acetylation, the mixture was cooled to ca. 0°, stirred with methanol for 15 minutes, and extracted with diethyl ether. The ether layer was washed sequentially with cold 2% aqueous hydrochloric acid and brine, dried over sodium sulfate, filtered, and concentrated in vacuo, affording 4.92 g of the title compound as a nearly analytically pure oil. nmr (CDCl$_3$): δ (ppm) 0.92 (t, 3H, propyl CH$_3$); 1.38 (s, 3H, 2-methyl CH$_3$); 2.31 (s, 3H, acetyl CH$_3$); 4.98 (m, 2H, alkenyl CH$_2$); 5.75 (m, 1H, alkenyl CH); 7.65, 7.72 (sets of d's, aromatic)

Analysis calcd. for C$_{19}$H$_{24}$O$_4$: C, 72.12; H, 7.65. Found: C, 71.54; H, 7.61.

EXAMPLE 3

7-acetoxy-2-(2-oxiranylethyl)-3,4-dihydro-2-methyl-8-propyl-2H-1-benzopyran-4-one

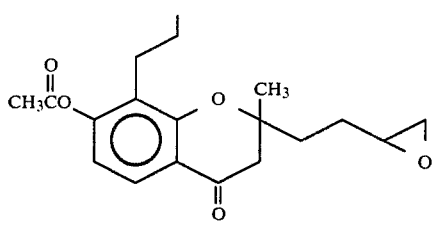

Epoxidation of 5.2 g (17.9 mmole) of the title product of Example 2 with 4.23 g (ca. 19.6 mmole) of 80% pure m-chloroperbenzoic acid in 50 ml of dichloromethane was initiated at 0°. The reaction mixture was allowed to stand at room temperature for nine hours. Water was added and the mixture was extracted with diethyl ether. The organic phase was washed successively with 5% aqueous sodium bicarbonate and 5% aqueous sodium sulfite, and then dried over magnesium sulfate, filtered, and concentrated in vacuo. Purification by high performance column chromatography afforded the title compound (5.73 g) as an oil, which was used in subsequent reactions without further purification.

nmr (CDCl$_3$): δ (ppm) 0.92 (t, 3H, propyl CH$_3$); 1.38 (s, 3H, 2-methyl CH$_3$); 2.32 (s, 3H, acetyl CH$_3$); 6.66, 7.72; (sets of d's, aromatic); Infrared (CHCl$_3$): 1762, 1690, 1598, 1429, 1100, 1020 cm$^{-1}$.

EXAMPLE 4

2-(2-oxiranylethyl)-3,4-dihydro-7-hydroxy-2-methyl-8-propyl-2H-1-benzopyran-4-one

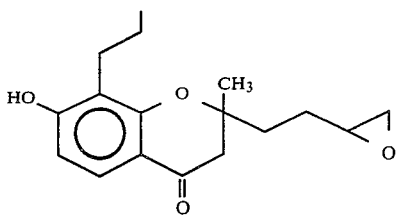

To a solution of 5.7 g of the title product of Example 3 in 80 ml of methanol was added 6 g of potassium carbonate. After stirring at room temperature, the mixture was concentrated in vacuo to a residue that was partitioned between water and ethyl acetate. The organic phase was concentrated to dryness and the residue redissolved in 1:1 (by volume) ethyl acetate-hexane. Filtration through a thick (ca. 7 cm) pad of silica gel and concentration of the filtrate afforded the title compound (4.29 g) as an oil, which was used in subsequent reactions without further purification.

nmr (CDCl$_3$): δ (ppm) 0.95 (t, 3H, propyl CH$_3$); 1.37 (s, 3H, 2-methyl CH$_3$); 6.45, 7.62 (sets of d's, aromatic); Infrared (CHCl$_3$): 3600, 3350, 1675, 1600, 1438, 1100, 1013 cm$^{-1}$.

EXAMPLE 5

3-(4-acetyl-3-hydroxy-2-propylphenoxy)propanol

A mixture of 10.1 g (52 mmole) of 2,4-dihydroxy-3-propylacetophenone, 4.7 ml (ca. 52 mmole) of 3-bromopropanol, 17.7 g (52 mmole) of tetrabutylammonium hydrogen sulfate, 34.6 ml (ca. 104 mmole) of 3N aqueous sodium hydroxide, and 100 ml of dichloromethane was stirred at reflux for 2.5 hours. Upon cooling, the organic phase was dried over magnesium sulfate, filtered, concentrated in vacuo, and purified by column chromatography on silica gel (using 5% by volume of ethyl acetate-toluene initially, followed by 50% ethyl acetate-toluene), affording 10.7 g of the title compound. The product was used in subsequent reactions without further purification.

nmr (CDCl$_3$): δ (ppm) 0.93 (t, 3H, propyl CH$_3$); 2.55 (s, 3H, acetyl CH$_3$); 3.86, 4.18 (set of t's, each 2H, OCH$_2$'s); 6.47, 7.60 (sets of d's, aromatic).

EXAMPLE 6

7-[3-(4-acetyl-3-hydroxy-2-propylphenoxy)propoxy]-2-(2-oxiranylethyl)-3,4-dihydro-2-methyl-8-propyl-2H-1-benzopyran-4-one To a solution of 4.16 g (14.3 mmole) of the title product of Example 4, 3.63 g (14.4 mmole) of the title product of Example 5, and 3.77 g (14.4 mmole) of triphenylphosphine in 40 ml of tetrahydrofuran was added 2.27 ml (ca. 14.5 mmole) of diethyl azodicarboxylate. After two days at room temperature, the mixture was concentrated in vacuo, dissolved in diethyl ether, and filtered through silica gel. The filtrate was concentrated and the residue purified by high performance column chromatography on silica gel (using ca. 10 to 20% by volume ethyl acetate-toluene as eluent). The initial eluate fractions, upon concentration, afforded 3.92 g of analytically pure title compound.

nmr (CDCl$_3$): δ (ppm) 0.90 (t, 6H, propyl CH$_3$'s); 1.36 (s, 3H, 2-methyl CH$_3$); 2.54 (s, 3H, acetyl CH$_3$); 4.23 (t, 4H, OCH$_2$'s); 6.47, 6.55, 7.56, 7.72 (sets of d's, aromatic).

Analysis calcd. for C$_{31}$H$_{40}$O$_7$: C, 70.97; H, 7.68. Found: C, 70.64; H, 7.77.

EXAMPLE 7

2-(4-acetoxy-3-hydroxybutyl)-7-[3-(4-acetyl-3-hydroxy-2-propylphenoxy)propoxy]-3,4-dihydro-2-methyl-8-propyl-2H-1-benzopyran-4-one and 2-(3-acetoxy-4-hydroxybutyl)-7-[3-(4-acetyl-3-hydroxy-2-propylphenoxy)propoxy]-3,4-dihydro-2-methyl-8-propyl-2H-1-benzopyran-4-one

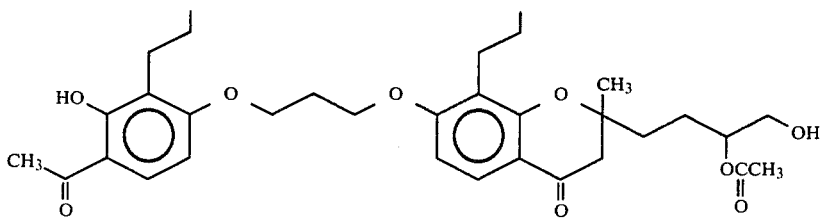

A solution of 3.9 g (7.4 mmole) of the title product of Example 6 and 0.61 g (7.2 mmole) of anhydrous sodium acetate in 63 ml of acetic acid was allowed to stand at room temperature for three days and at 45° for another two days. After concentrating in vacuo, the reaction mixture was chromatographed on silica gel (using ethyl acetate-toluene as eluant), giving 3.4 g of a ca. 2:1 mixture of the "4-acetoxy" and "3-acetoxy" position isomers of the title compounds. The isomeric mixture was used in subsequent reactions without further purification.

nmr (CDCl$_3$): δ (ppm) 0.89 (t, 6H, propyl CH$_3$'s); 1.35 (s, 3H, 2-methyl CH$_3$); 2.07 (s, ca. 2H, "4-acetoxy" isomer) plus 2.03 (s, ca. 1H, "3-acetoxy" isomer); 2.54 (s, 3H, acetyl CH$_3$); 3.5–4.3 (m's, 7H, OCH$_2$'s and OCH); 6.41, 6.53, 7.55, 7.70 (sets of d's, aromatic).

Analysis calcd. for C$_{33}$H$_{44}$O$_9$: C, 67.79; H, 7.58. Found: C, 67.35; H, 7.61.

ate, dried over magnesium sulfate, filtered, and concentrated in vacuo. The residue was purified by chromatography on a silica-gel coated spinning disk (using ethyl acetate-hexane as eluent). The initial eluate fractions, upon concentration, yielded 419 mg of the title compound, m.p. 114°–117°. Recrystallization from ethyl acetate-cyclohexane afforded analytically pure title compound, m.p. 118°–120°.

nmr (CDCl$_3$): δ (ppm) 0.89 (t, 6H, propyl CH$_3$'s); 1.33 (s, 3H, 2-methyl CH$_3$); 2.15 (s, 3H, acetoxy CH$_3$); 2.55 (s, 3H, acetyl CH$_3$); 4.22 (t, 4H, OCH$_2$'s); 4.64 (s, 2H, CO-CH$_2$O); 6.40, 6.53, 7.55, 7.70 (sets of d's, aromatic).

Analysis calcd. for C$_{33}$H$_{42}$O$_9$: C, 68.02; H, 7.26. Found: C, 67.86; H, 7.31.

EXAMPLE 9

2-acetoxy-4-[7-[3-(4-acetyl-3-hydroxy-2-propylphenoxy)propoxy]-3,4-dihydro-2-methyl-4-oxo-8-propyl-2H-1-benzopyran-2-yl]butanoic acid

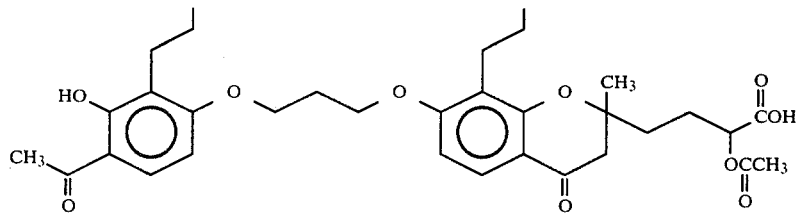

EXAMPLE 8

2-(4-acetoxy-3-oxobutyl)-7-[3-(4-acetyl-3-hydroxy-2-propylphenoxy)propoxy]-3,4-dihydro-2-methyl-8-propyl-2H-1-benzopyran-4-one The title compound is isolated from the aqueous bicarbonate wash described in Example 8 by acidification (pH 3) with dilute hydrochloric acid, extraction into diethyl ether, and concentration to dryness.

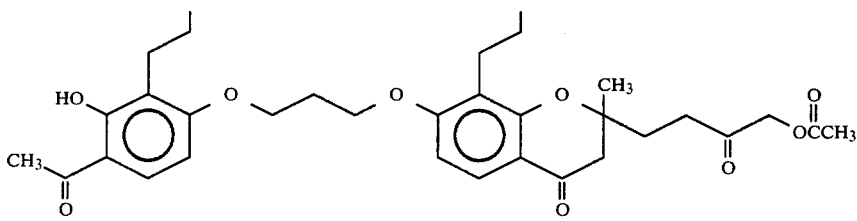

To a cold (0°) solution of 1.0 g (2 mmole) of the product mixture of Example 7 in 5 ml of acetone was added 0.43 ml of 8N Jones reagent. After the mixture was warmed to room temperature, water was added and the crude product was extracted into diethyl ether. The organic phase was washed with 2% aqueous sodium bicarbon-

EXAMPLE 10

7-[3-(4-acetyl-3-hydroxy-2-propylphenoxy)propoxy]-3,4-dihydro-2-(4-hydroxy-3-oxobutyl)-2-methyl-8-propyl-2H-1-benzopyran-4-one hemihydrate

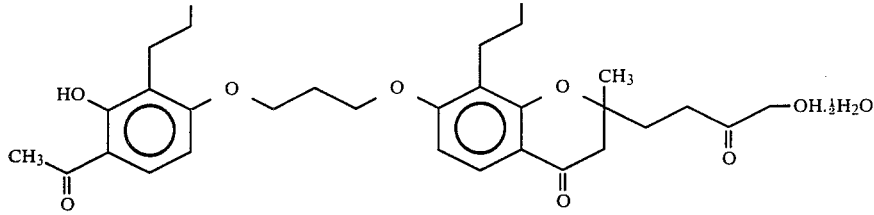

A mixture of 268 mg of the title product of Example 8 and 191 mg of potassium carbonate was stirred at 0° in 7 ml of methanol. After one hour 0.70 ml of acetic acid and 30 ml of water were added, and the mixture was extracted with diethyl ether. The organic phase was washed with brine, dried over magnesium sulfate, filtered, and concentrated in vacuo. Purification by chromatography on a silica-gel coated spinning disk (using 60:40:1 by volume ethyl acetate-hexane-acetic acid as eluent) afforded 164 mg of analytically pure title compound.

nmr (CDCl$_3$): δ (ppm) 0.89 (t, 6H, propyl CH$_3$'s); 1.40 (s, 3H, 2-methyl CH$_3$); 2.54 (s, 3H, acetyl CH$_3$); 4.23 (t, 4H, OCH$_2$'s); 6.41, 6.54, 7.55, 7.74 (sets of d's, aromatic).

Analysis calcd. for C$_{31}$H$_{40}$O$_9$·1/2H$_2$O: C, 67.76; H, 7.52. Found: C, 67.93; H, 7.65.

EXAMPLE 11

4-[7-[3-(4-acetyl-3-hydroxy-2-propylphenoxy)propoxy]-3,4-dihydro-2-methyl-4-oxo-8-propyl-2H-1-benzopyran-2-yl]-2-hydroxybutanoic acid

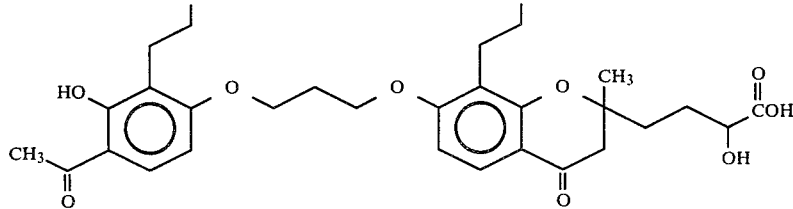

The title product of Example 9 is saponified by stirring for four hours with 2% sodium hydroxide in 50% by volume aqueous methanol. The mixture is acidified (pH 3) with dilute aqueous hydrochloric acid and extracted into diethyl ether. Concentration of the ether layer affords the title compound.

EXAMPLE 12

7-[3-(4-acetyl-3-hydroxy-2-propylphenoxy)propoxy]-3,4-dihydro-2-(3,4-dihydroxybutyl)-2-methyl-8-propyl-2H-1-benzopyran-4-one hydrate

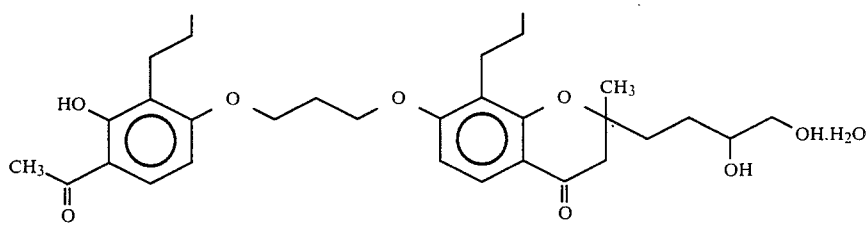

To a solution of 500 mg of the product mixture described in Example 7 in 3 ml of methanol was added a solution of 144 mg of lithium hydroxide in 1 ml of water. After standing overnight at room temperature, the reaction mixture was diluted with water and extracted with ethyl acetate. The organic phase was washed with brine, dried over magnesium, filtered, and concentrated in vacuo. Purification by chromatography on a silica-gel coated spinning disk (using 50:50:8 by volume ethyl acetate-cyclohexane-acetic acid as eluent) afforded 331 mg of analytically pure title compound.

nmr (CDCl$_3$): δ (ppm) 0.90 (t, 6H, propyl CH$_3$'s); 1.36 (s, 3H, 2-methyl CH$_3$); 2.55 (s, 3H, acetyl CH$_3$); ca. 3.5 (m, -CHOH-CH$_2$OH and H$_2$O); 4.22 (t, 4H, OCH$_2$'s); 6.42, 6.53, 7.55, 7.69 (sets of d's, aromatic).

Analysis calcd. for C$_{31}$H$_{42}$O$_8$·H$_2$O: C, 66.41; H, 7.91. Found: C, 66.09; H, 7.85.

EXAMPLE 13

3-(7-acetoxy-3,4-dihydro-2-methyl-4-oxo-8-propyl-2H-1-benzopyran-2-yl)propanal

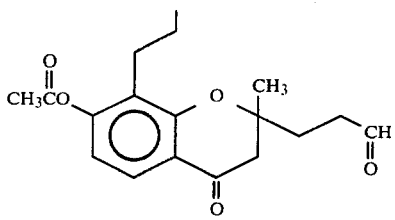

To a solution of 3.16 g (10 mmole) of the title product of Example 2 in 60 ml of t-butyl alcohol is added a solution of 4.5 g (21 mmole) of sodium periodate in 15 ml of water and 10 mg of osmium tetroxide. After about four hours the reaction mixture is filtered to remove sodium iodate and the filtrate concentrated in vacuo. The residue is dissolved in diethyl ether, washed sequentially with 2% aqueous sodium sulfite and brine, dried over magnesium sulfate, filtered, and concentrated in vacuo. The crude title compound is used immediately in subsequent reactions.

EXAMPLE 14

7-acetoxy-2-(3-pentenyl)-3,4-dihydro-2-methyl-8-propyl-2H-1-benzopyran-4-one

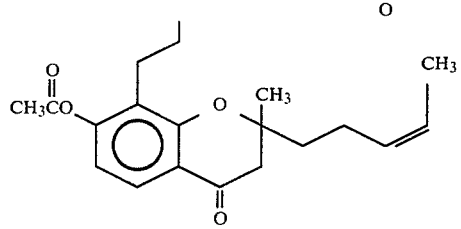

To a cold (0°) suspension of 4.5 g (12 mmole) of ethyltriphenylphosphonium bromide in 70 ml of dry tetrahydrofuran is added 7.5 ml (ca. 12 mmole) of 1.6M butyllithium in hexane. After one hour the resultant phosphorane solution is diluted with 40 ml of dimethylsulfoxide and cooled to −20°. Approximately 3.0 g of the title product of Example 13 is added, and the mixture is stirred at −20° for about one hour and then allowed to warm to room temperature. Upon adding 1.0 ml of acetic acid, the mixture is diluted with 150 ml of diethyl ether, washed with brine, dried over magnesium sulfate, filtered, and concentrated in vacuo. Purification by chromatography on silica gel affords the title compound.

EXAMPLE 15

2-(3-methyloxiran-2-yl)ethyl]-3,4-dihydro-7-hydroxy-2-methyl-8-propyl-2H-1-benzopyran-4-one

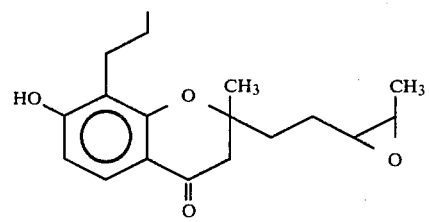

The title compound is prepared from the title product of Example 14 by the general methods described in Examples 3 and 4.

EXAMPLE 16

7-[3-(4-acetyl-3-hydroxy-2-propylphenoxy)propoxy]-2-[2-(3-methyloxiran-2-yl)ethyl]-3,4-dihydro-2-methyl-8-propyl-2H-1-benzopyran-4-one

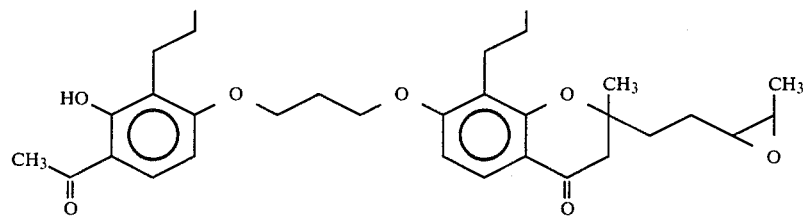

The title compound is prepared from the title product of Example 15 by the general method described in Example 6.

EXAMPLE 17

2-(4-acetoxy-3-hydroxypentyl)-7-[3-(4-acetyl-3-hydroxy-2-propylphenoxy)propoxy]-3,4-dihydro-2-methyl-8-propyl-2H-1-benzopyran-4-one

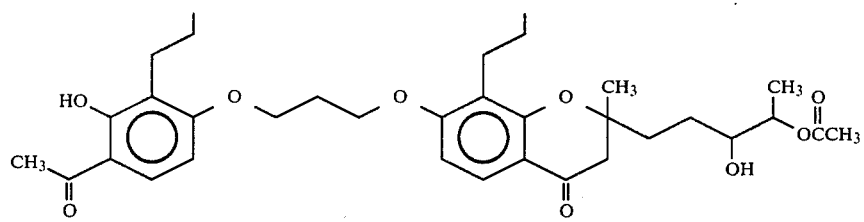

and 2-(3-acetoxy-4-hydroxypentyl)-7-[3-(4-acetyl-3-hydroxy-2-propylphenoxy)propoxy]-3,4-dihydro-2-methyl-8-propyl-2H-1-benzopyran-4-one

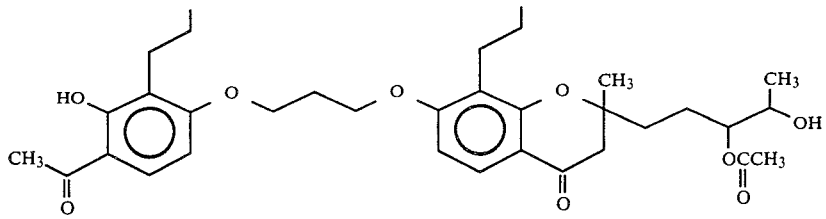

The title product mixture is prepared by a method similar to that described in Example 7, except for using a solution of benzyltrimethylammonium hydroxide and acetic acid in dimethylformamide instead of sodium acetate in acetic acid. The product mixture is used in subsequent reactions without further purification.

EXAMPLE 18

7-[3-(4-acetyl-3-hydroxy-2-propylphenoxy)propoxy]-3,4-dihydro-2-(3,4-dihydroxypentyl)-2-methyl-8-propyl-2H-1-benzopyran-4-one

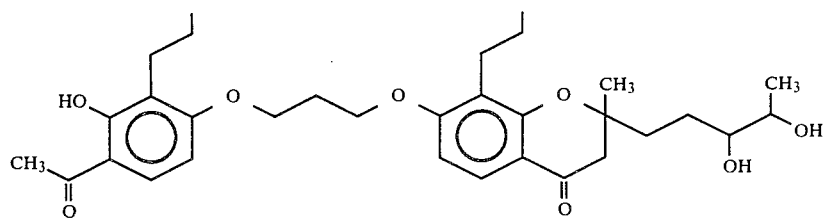

The title compound is prepared by the method of Example 12 from the title product mixture of Example 17.

EXAMPLE 19

2-(4-acetoxy-3-oxopentyl)-7-[3-(4-acetyl-3-hydroxy-2-propylphenoxy)propoxy]-3,4-dihydro-2-methyl-8-propyl-2H-1-benzopyran-4-one

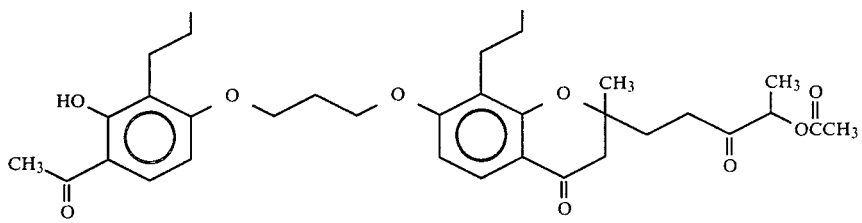

and 2-(3-acetoxy-4-oxopentyl)-7-[3-(4-acetyl-3-hydroxy-2-propylphenoxy)propoxy]-3,4-dihydro-2-methyl-8-propyl-2H-1-benzopyran-4-one

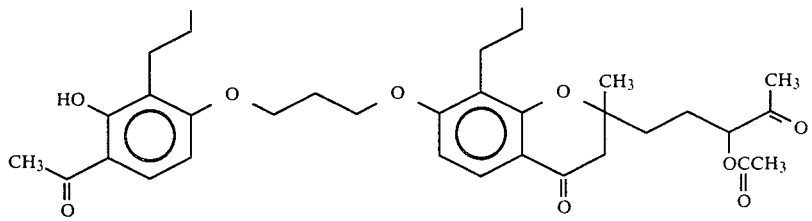

The title compounds are prepared by the general method described in Example 8. The chromatographic purification partially separates the two position isomer title compounds.

EXAMPLE 20

7-[3-(4-acetyl-3-hydroxy-2-propylphenoxy)propoxy]-3,4-dihydro-2-(4-hydroxy-3-oxopentyl)-2-methyl-8-propyl-2H-1-benzopyran-4-one

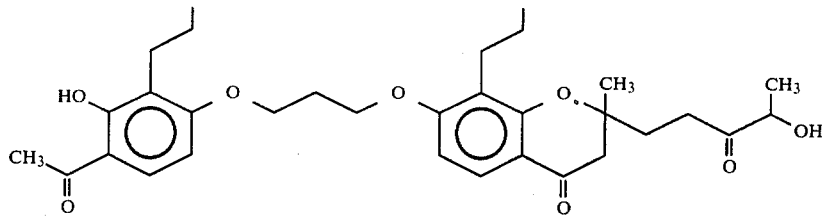

Using the method described in Example 10, the isolates of chromatographic fractions of Example 19 containing predominantly the "4-acetoxy" position isomer are saponified. Chromatographic purification affords the title compound.

EXAMPLE 21

7-[3-(4-acetyl-3-hydroxy-2-propylphenoxy)propoxy]-3,4-dihydro-2-(3-hydroxy-4-oxopentyl)-2-methyl-8-propyl-2H-1-benzopyran-4-one

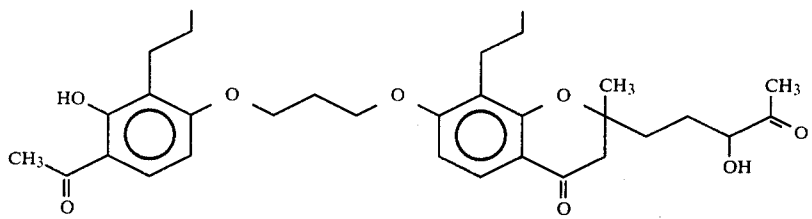

Using the method described in Example 10, the isolates of chromatographic fractions of Example 19 containing predominantly the "3-acetoxy" position isomer are saponified. Chromatographic purification affords the title compound.

EXAMPLE 22

7-[3-(4-acetyl-3-hydroxy-2-propylphenoxy)-2-hydroxypropoxy]-2-(3-butenyl)-3,4-dihydro-2-methyl-8-propyl-2H-1-benzopyran-4-one

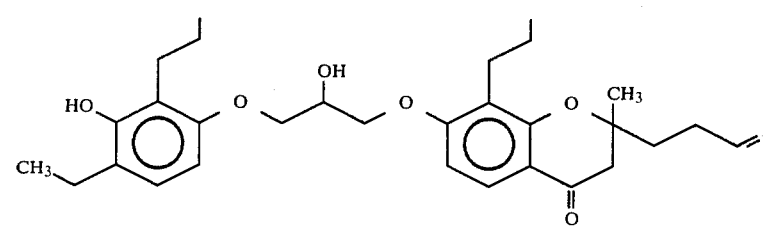

To a solution of 5.5 g (20 mmole) of the title product of Example 1 and 7.5 g (30 mmole) of 2-hydroxy-4-(2-oxiranylethyl)-3-propylacetophenone in 60 ml of dry dimethylformamide is added two drops of benzyltrimethylammonium hydroxide. The mixture is heated at 110°–120° for about two days, then cooled and concentrated in vacuo to dryness. Purification by column chromatography on silica gel (using acetone-hexane as eluent) affords the title compound.

EXAMPLE 23

7-[3-(4-acetyl-3-hydroxy-2-propylphenoxy)-2-hydroxypropoxy]-3,4-dihydro-2-(3,4-dihydroxybutyl)-2-methyl-8-propyl-2H-1-benzopyran-4-one

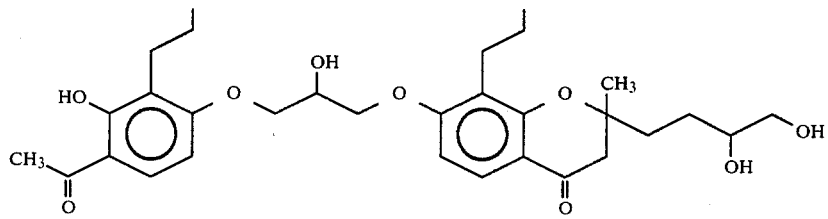

To a solution of 7.8 g (15 mmole) of the title product of Example 22 in 100 ml of 3:3:1 (by volume) of t-butyl alcohol-acetone-water is added 2.2 g (16 mmole) of 4-methylmorpholine N-oxide monohydrate and 10 mg of osmium tetroxide. After stirring overnight at room temperature, the mixture is concentrated in vacuo. The residue is taken up in diethyl ether, washed successively with dilute aqueous hydrochloric acid and water, dried over magnesium sulfate, filtered, and concentrated in vacuo. Purification by chromatography on a silica-gel coated spinning disk affords the title compound.

EXAMPLE 24

7-[3-(4-acetyl-3-hydroxy-2-propylphenoxy)-2-oxo-propoxy]-3,4-dihydro-2-(4-hydroxy-3-oxobutyl)-2-methyl-8-propyl-2H-1-benzopyran-4-one

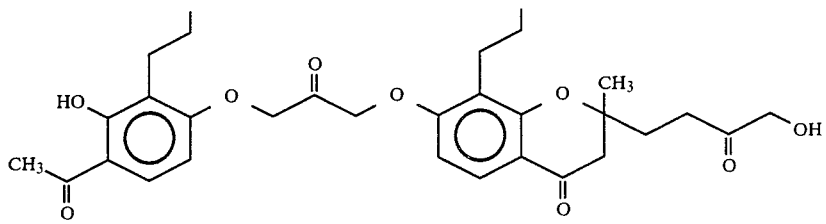

A solution of 5.6 g (10 mmole) of the title product of Example 23 and 3.1 g (11 mmole) of triphenylmethyl chloride (trityl chloride) in 50 ml of dry pyridine is heated at 100° for about three hours. Upon cooling, about 5 ml of water is added and the mixture is concentrated in vacuo to a thick oil, which is triturated with three portions of water, carefully decanting the supernatant each time. The residue is dried thoroughly under vacuum. The crude intermediate product, in which the primary alcohol function of the starting material is protected by a trityl group, is used in the subsequent oxidation reaction without further purification. Oxidation of the two secondary alcohol functions is effected by the method described in Example 8, except that 4.0 ml of 8N Jones reagent is employed. The residue was purified by chromatography on a silica-gel coated spinning disk (using ethyl acetate-hexane as eluent). The purified trityl-protected intermediate is stirred in 40 ml of a ca. 3:1 mixture by volume of 90% aqueous trifluoroacetic acid and t-butyl alcohol. After five minutes the mixture is neutralized with dilute aqueous sodium bicarbonate and concentrated in vacuo. The residue is taken up in ethyl acetate, washed sequentially with water and brine, dried over magnesium sulfate, filtered, and concentrated to dryness. Purification by chromatography on a silica-gel coated spinning disk affords the title compound.

What is claimed is:

1. A compound of the formula:

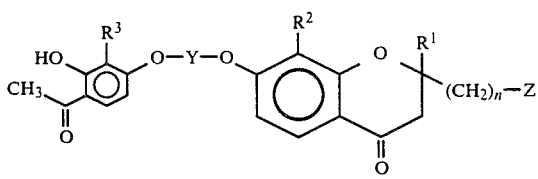

wherein Y is:

(a) —$(CH_2)_m$—
(b) —$(CH_2)_p$—CHOH—$(CH_2)_q$—
(c) —$(CH_2)_r$—CO—$(CH_2)_s$— wherein Z is:

(a)

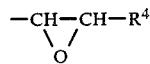

(b)

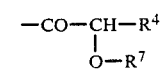

(c)

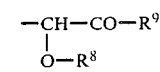

(d)

—CH—CO—$R^9$
  |
  O—$R^8$ wherein $R^1$, $R^2$, and $R^3$ are alkyl of 1 to 6 carbon atoms, inclusive, each being the same or different;
wherein $R^4$ is:
  (a) hydrogen; or
  (b) alkyl of 1 to 6 carbon atoms, inclusive;
wherein $R^5$ and $R^6$, each being the same or different, are:
  (a) hydrogen; or
  (b) alkanoyl of 2 to 6 carbon atoms, inclusive;
wherein $R^7$ and $R^8$ are:
  (a) hydrogen; or
  (b) alkanoyl of 2 to 6 carbon atoms, inclusive;
wherein $R^9$ is alkyl of 1 to 6 carbon atoms, inclusive;
wherein n is an integer from 1 to 10, inclusive;
wherein m is an integer from 2 to 7, inclusive;
wherein each of p and q is an integer from 1 to 5, inclusive, with the proviso that the sum (p+q) is no greater than 6;
wherein each of r and s is an integer from 1 to 5, inclusive, with the proviso that the sum (r+s) is no greater than 6.

2. A compound according to claim 1 having the formula:

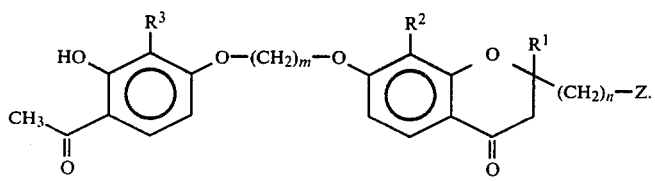

3. A compound according to claim 2 having the formula:

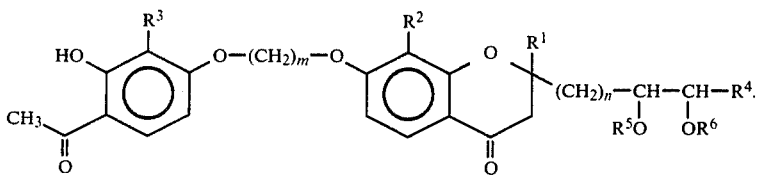

4. A compound according to claim 3, which is 7-[3-(4-acetyl-3-hydroxy-2-propylphenoxy)propoxy]-3,4-dihydro-2-(3,4-dihydroxybutyl)-2-methyl-8-propyl-2H-1-benzopyran-4-one.

5. A compound according to claim 3, which is 7-[3-(4-acetyl-3-hydroxy-2-propylphenoxy)propoxy]-3,4-dihydro-2-(3,4-dihydroxypentyl)-2-methyl-8-propyl-2H-1-benzopyran-4-one.

6. A compound according to claim 3, which is 2-(4-acetoxy-3-hydroxybutyl)-7-[3-(4-acetyl-3-hydroxy-2-propylphenoxy)-propoxy]-3,4-dihydro-2-methyl-8-propyl-2H-1-benzopyran-4-one.

7. A compound according to claim 3, which is 2-(4-acetoxy-3-hydroxypentyl)-7-[3-(4-acetyl-3-hydroxy-2-propylphenoxy)-propoxy]-3,4-dihydro-2-methyl-8-propyl-2H-1-benzopyran-4-one.

8. A compound according to claim 3, which is 2-(3-acetoxy-4-hydroxybutyl)-7-[3-(4-acetyl-3-hydroxy-2-propylphenoxy)-propoxy]-3,4-dihydro-2-methyl-8-propyl-2H-1-benzopyran-4-one.

9. A compound according to claim 3, which is 2-(3-acetoxy-4-hydroxypentyl)-7-[3-(4-acetyl-3-hydroxy-2-propylphenoxy)-propoxy]-3,4-dihydro-2-methyl-8-propyl-2H-1-benzopyran-4-one.

10. A compound according to claim 2 having the formula:

11. A compound according to claim 10, which is 7-[3-(4-acetyl-3-hydroxy-2-propylphenoxy)propoxy]-3,4-dihydro-2-(4-hydroxy-3-oxobutyl)-2-methyl-8-propyl-2H-1-benzopyran-4-one.

12. A compound according to claim 10, which is 7-[3-(4-acetyl-3-hydroxy-2-propylphenoxy)propoxy]-3,4-dihydro-2-(4-hydroxy-3-oxopentyl)-2-methyl-8-propyl-2H-1-benzopyran-4-one.

13. A compound according to claim 10, which is 2-(4-acetoxy-3-oxobutyl)-7-[3-(4-acetyl-3-hydroxy-2-propylphenoxy)-propoxy]-3,4-dihydro-2-methyl-8-propyl-2H-1-benzopyran-4-one.

14. A compound according to claim 10, which is 2-(4-acetoxy-3-oxopentyl)-7-[3-(4-acetyl-3-hydroxy-2-propylphenoxy)-propoxy]-3,4-dihydro-2-methyl-8-propyl-2H-1-benzopyran-4-one.

15. A compound according to claim 2 having the formula:

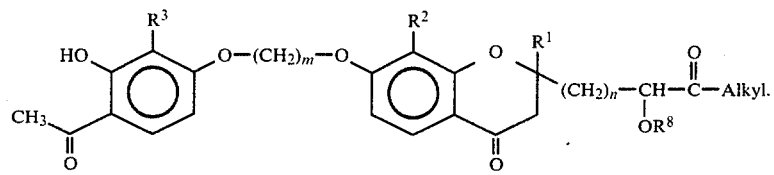

16. A compound according to claim 15, which is 7-[3-(4-acetyl-3-hydroxy-2-propylphenoxy)propoxy]-3,4-dihydro-2-(3-hydroxy-4-oxopentyl)-2-methyl-8-propyl-2H-1-benzopyran-4-one.

17. A compound according to claim 15, which is 2-(3-acetoxy-4-oxopentyl)-7-[3-(4-acetyl-3-hydroxy-2-propylphenoxy)-propoxy]-3,4-dihydro-2-methyl-8-propyl-2H-1-benzopyran-4-one.

18. A compound according to claim 2 having the formula:

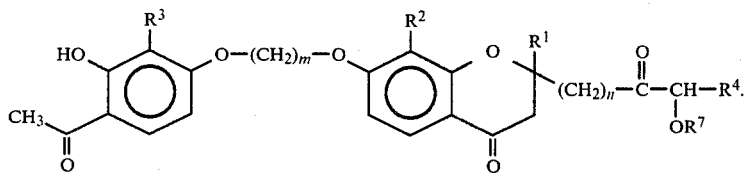

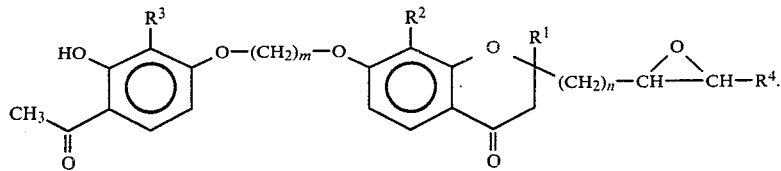

19. A compound according to claim 18, which is 7-[3-(4-acetyl-3-hydroxy-2-propylphenoxy)propoxy]-2-(2-oxiranylethyl)-3,4-dihydro-2-methyl-8-propyl-2H-1-benzopyran-4-one.

20. A compound according to claim 18, which is 7-[3-(4-acetyl-3-hydroxy-2-propylphenoxy)propoxy]-2-[2-(3-methyloxiran-2-yl)ethyl]-3,4-dihydro-2-methyl-8-propyl-2H-1-benzopyran-4-one

21. A compound according to claim 1 having the formula:

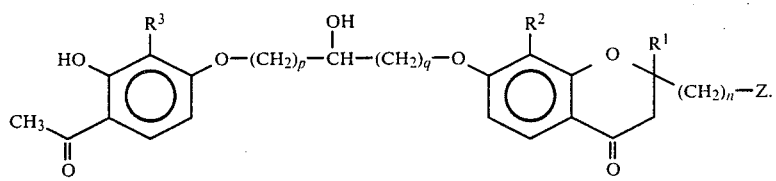

22. A compound according to claim 21 having the formula:

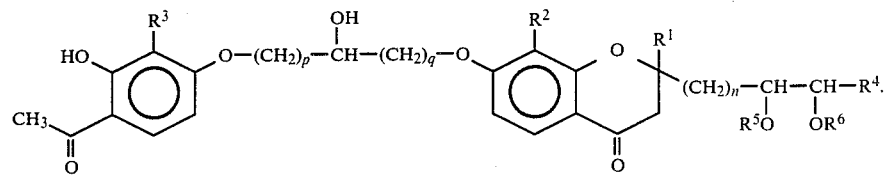

23. A compound according to claim 22, which is 7-[3-(4-acetyl-3-hydroxy-2-propylphenoxy)-2-hydroxypropoxy]-3,4-dihydro-2-(3,4-dihydroxybutyl)-2-methyl-8-propyl-2H-1-benzopyran-4-one.

24. A compound according to claim 1 having the formula:

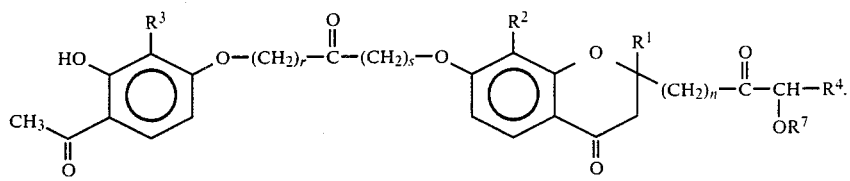

25. A compound according to claim 24, which is 7-[3-(4-acetyl-3-hydroxy-2-propylphenoxy)-2-oxopropoxy]-3,4-dihydro-2-(4-hydroxy-3-oxobutyl)-2-methyl-8-propyl-2H-1-benzopyran-4-one.

* * * * *